United States Patent [19]

Kimura

[11] Patent Number: 4,984,748
[45] Date of Patent: Jan. 15, 1991

[54] WASTE STERILIZING AND CRUSHING APPARATUS

[75] Inventor: Ikuo Kimura, Hyogo, Japan

[73] Assignee: Kyokuto Kaihatsu Kogyo Co., Ltd., Nishinomiya, Japan

[21] Appl. No.: 489,911

[22] Filed: Mar. 9, 1990

[30] Foreign Application Priority Data

Mar. 13, 1989 [JP] Japan ................................. 28331[U]
Mar. 13, 1989 [JP] Japan ............................... 1-28332 [U]
Sep. 29, 1989 [JP] Japan ............................. 1-115696 [U]

[51] Int. Cl.⁵ ............................................. B02C 19/00
[52] U.S. Cl. ...................................... 241/65; 241/100
[58] Field of Search ..................... 241/65, 99, 100, 243

[56] References Cited

U.S. PATENT DOCUMENTS 4,487,372 12/1984 Deve ...................................... 241/65
4,860,958 8/1989 Yerman .............................. 241/65 X
4,905,916 3/1990 Sorwic et al. ..................... 241/65 X Primary Examiner—Timothy V. Eley
Attorney, Agent, or Firm—Armstrong, Nikaido Marmelstein, Kubovcik and Murray

[57] ABSTRACT

A waste sterilizing and crushing apparatus includes a heating chamber adapted to receive wastes therein, and a heater for heating the interior of the heating chamber. The bottom of the heating chamber is formed with a discharge port, and a cover plate driven by a driving device to open and close the discharge port. A crusher is disposed below the heating chamber for crushing wastes, and a feeder is provided whereby wastes discharged through the discharge port are fed into the crusher. When the wastes are heated in the heating chamber, the discharge port is opened by the action of the cover plate. Thereupon, the wastes in the heating chamber are charged into the crusher through the discharge port and feeder.

6 Claims, 14 Drawing Sheets

WASTE STERILIZING AND CRUSHING APPARATUS

BACKGROUND OF THE INVENTION

This invention relates to a waste sterilizing and crushing apparatus and more particularly it relates to an apparatus which, when it is desired to dispose of medical wastes, such as disposable injectors and the like, heats said wastes for sterilization and then crushes them.

For example, in hospitals, disposable injectors and drip infusion containers are discarded after use. Further, experimental animals, such as rats, are used and their dead bodies are discarded.

The various wastes described above usually contain disease causing germs. Thus, it has been suggested to sterilize the wastes by chemicals.

Wastes from hospitals are buried in a land to be reclaimed, but if their bulk is great, it sometimes occurs that they cannot be buried directly in such land. Thus, it is contemplated to crush said wastes to minimize their bulk.

However, if wastes are treated with chemicals for sterilization, it becomes difficult to treat these chemicals themselves after use.

When wastes are to be crushed, crushing conditions differ to a large extent from wastes to wastes; some wastes, such as injectors, are solid, and others, such as dead bodies of rats, are soft, containing water. Therefore, if a single type of crusher is used to crush all these wastes, a desired crushing effect would not be obtained.

SUMMARY OF THE INVENTION

A first object of the invention is to attain effective sterilization without using a chemical. It is also intended to attain sufficient crushing even if crushing conditions differ when some wastes are rigid and others are soft, containing water. It is also intended to effect sterilization and crushing in an automatic manner without the wastes coming in contact with the operator's hands.

A second object of the invention is to provide an arrangement which performs said sterilizing and crushing operations easily and quickly.

A third object of the invention is to provide a waste treating apparatus of compact construction.

BRIEF DESCRIPTION OF THE DRAWINGS

FIG. 1 is a side view, in section, of a waste sterilizing and crushing apparatus;
FIG. 2 is a front view, in section, of the upper portion of said apparatus;
FIG. 3 is a plan view, in section, of the upper portion of said apparatus;
FIG. 4 is an exploded perspective view of a portion of said apparatus;
FIG. 5 is a complete perspective view of said apparatus;
FIG. 6 is a side view, in section, of said apparatus;
FIG. 7 is a detailed sectional view showing a portion of FIG. 6 on an enlarged scale;
FIG. 8 is a front view, in section, of the portion shown in FIG. 7;
FIG. 9 is an exploded perspective view of the portion shown in FIG. 7;
FIG. 10 is a complete perspective view of said apparatus;
FIG. 11 is a side view, in section, of said apparatus;
FIG. 12 a front view, in section, of said apparatus;
FIG. 13 is a plan view, partly in section, of said apparatus;
and FIG. 14 is a complete perspective view of said apparatus.

DETAILED DESCRIPTION OF THE PREFERRED EMBODIMENTS

Figure 1:
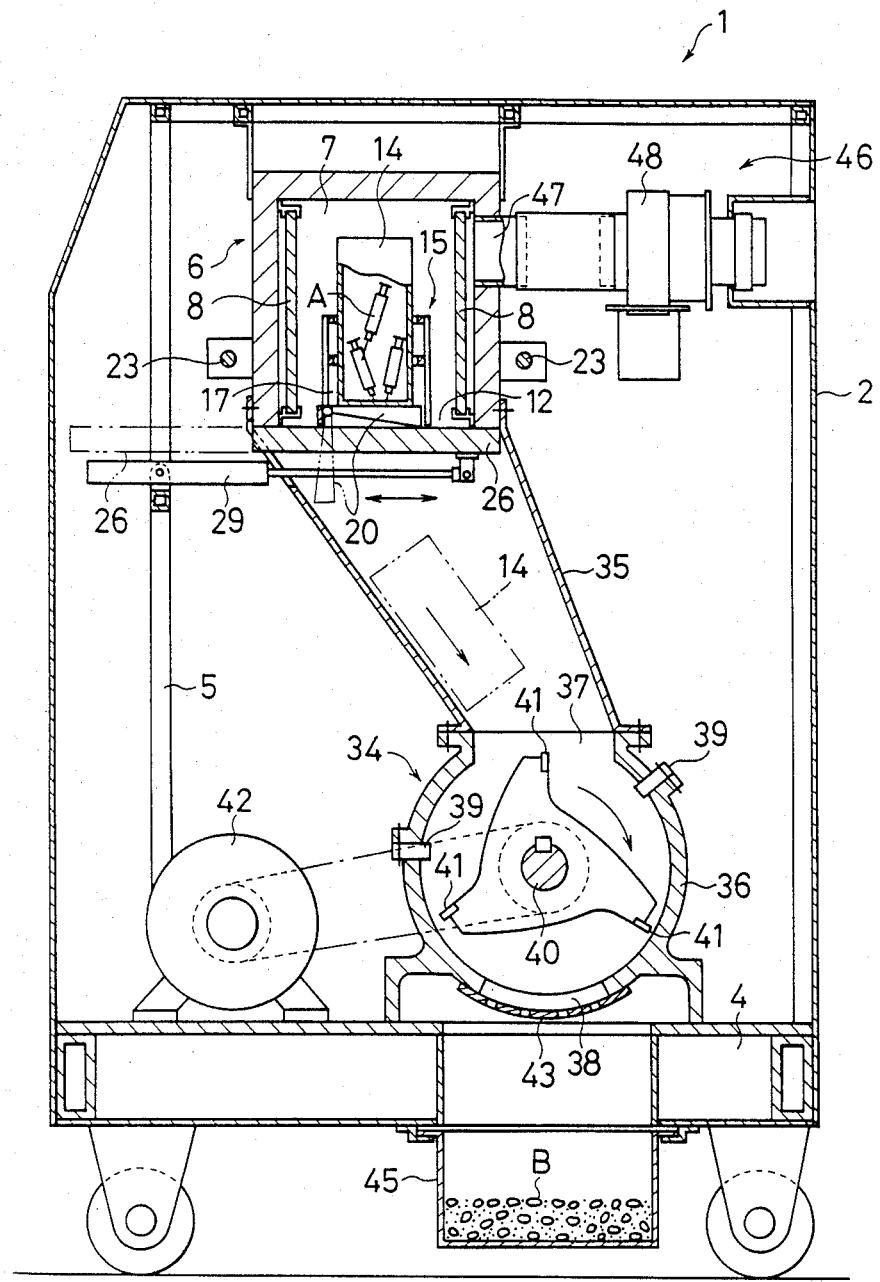
FIGS. 1 through 5 show a first embodiment of the invention.

FIGS. 1 through 5 show a first embodiment of the invention.

In these figures, a sterilizing and crushing apparatus 1 has a box-like casing 2 of sheet metal mounted on a carriage 4 movable on a working floor surface 3. Further, said casing 2 is reinforced by an internally disposed frame 5.

In the upper portion of said casing 2, a heat insulating box 6 is attached to said frame 5, said heat insulating box 6 serving as a heating chamber 7 adapted to receive wastes A. A heater 8, which is a far infrared heater, is attached to the inner wall surface of said heat insulating box 6 to heat the interior of the heating chamber 7.

An inlet opening 10 is formed in the upper lateral wall surface of said casing 2, while an insertion port 11 corresponding to said inlet opening 10 is formed in the lateral wall of the heat insulating box 6. Further, a discharge port 12 is formed in the bottom of said heat insulating box 6.

On the other hand, containers 14 made of incombustible material are provided for charging said wastes A, and a drawer box 15 is provided for charging said containers 14. The lateral wall of the drawer box 15 is defined by a metal frame 16 which is rectangular in plan view and adapted to receive said containers 14. The bottom of said metal frame 16 is formed with a communication port 17 corresponding to said discharge port 12. A bracket plate 18 is attached to the lower side of said metal frame 16, and an operatively associated cover 20 is turnably attached to said bracket plate 18 by a pair of hinges 19, said operating cover 20 being formed with a number of through-holes 21, as shown in FIG. 3.

A lid 22 is provided for simultaneously opening and closing said inlet opening 10 and insertion port 11, said lid 22 being attached to one end of said drawer box 15. A pair of guide rods 23 extend from the lid 22 along the metal frame 16. The guide rods 23 are slidably fitted in support pipes 24 attached to the outer lateral wall surface of the heat insulating box 6. That is, the drawer box 15 and lid 22 are slidably supported by the heat insulating box 6. A handle 25 is formed on the outer surface of said lid 22. When the operator holds the handle 25 and pushes or pulls the lid 22 to slide the guide rods 23 in the support pipes 24, the other end of the drawer box 15 is taken in or out of the heating chamber 7 through said inlet opening 10 and insertion port 11. When the drawer box 15 is inserted into the heating chamber 7, said lid 22 closes the inlet opening 10 and insertion port 11.

Figure 2:
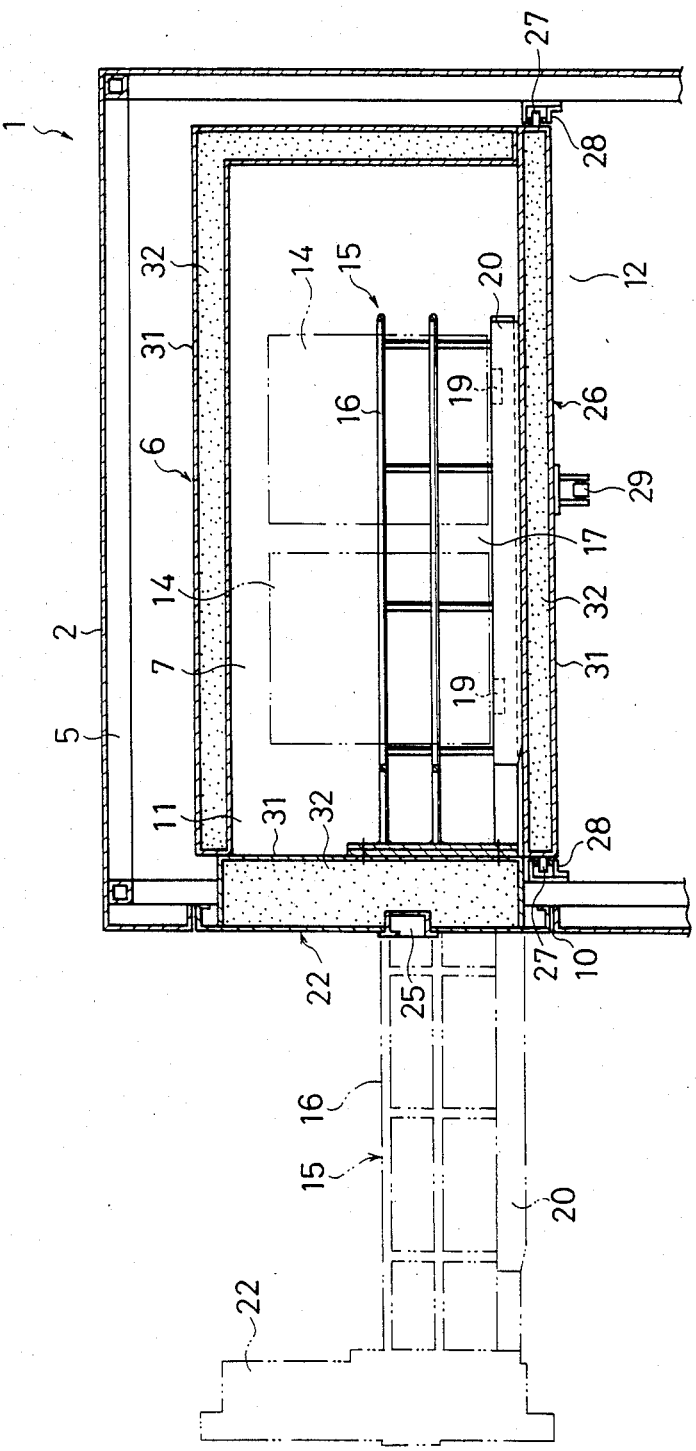
Figure 3:
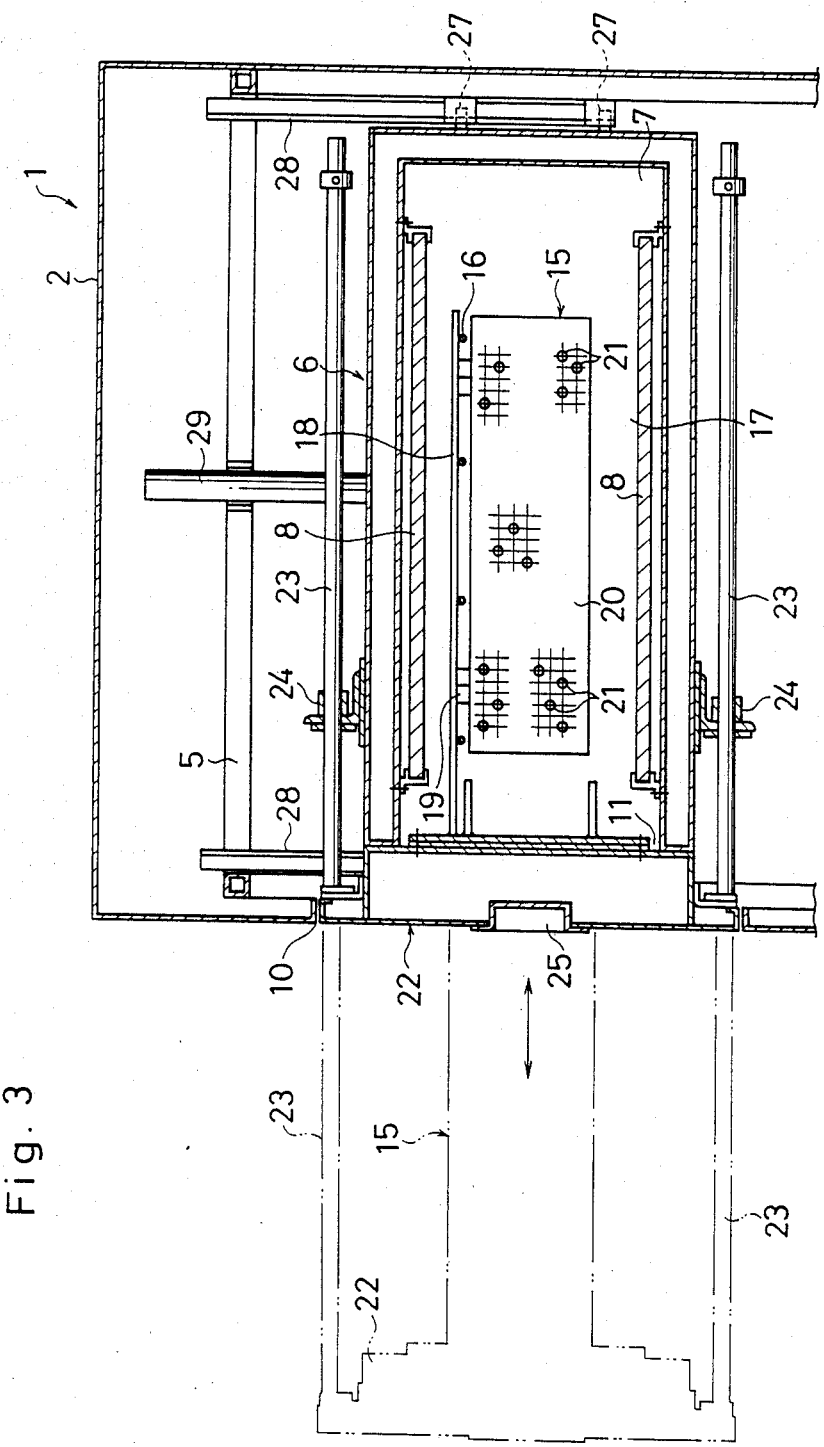

In FIGS. 2 and 3, the phantom lines indicate the drawer box 15 drawn out of the heating chamber 7. In this case, containers 14 having wastes A received therein can be charged into the drawer box 15 from the outside of the sterilizing and crushing apparatus 1. In said figures, the solid lines indicate the drawer box 15 inserted in the heating chamber 7. In this case, wastes A and containers 14 are inserted into the heating chamber 7 together with the drawer box 15.

That is, since the insertion of wastes A into the heating chamber 7 is effected through the inlet opening 10 formed in the lateral wall of the casing 2, the inserting operation can be effected in a lower place and hence is easier than when wastes A are charged from above the casing 2. Furthermore, when the drawer box 15 having wastes A received therein is inserted into the heating chamber 7, the lid 22 automatically closes the insertion port 11, eliminating the need for a separate operation for closing the insertion port 11. Therefore, the operation for inserting wastes A becomes easier by the corresponding amount and can be effected in a shorter time.

A cover plate 26 is disposed below the heat insulating chamber 6 so that said discharge port 12 can be opened and closed. A pair of slide pins 27 project from each of the opposite lateral surfaces of the cover plate 26. On the other hand, a pair of guide rails 28 are installed to extend in a direction orthogonal to the direction of insertion or withdrawal of the drawer box 15, as seen in plan view, said guide rails 28 being supported by the frame 5.

The slide pins 27 are slidably fitted in the guide rails 28, whereby the cover plate 26 can be horizontally slid along the guide rails 28. Further, an air cylinder 29, which is driving means driven by fluid such as air, is pivotally mounted on the frame 5, said air cylinder 29 being adapted to actuate said cover plate 26.

And when the air cylinder 29 is actuated by fluid pressure to extend as shown in solid lines in FIG. 1, the cover plate 26 is slid along the guide rails 28, closing the discharge port 12. Further, at this time, the operatively associated cover 20 is pushed by said cover plate 26 to turn upward, thus closing the communication port 17.

Reversely, when the air cylinder 29 is contracted by fluid pressure, the cover plate 26 is slid along the guide rails, as shown in phantom lines in FIG. 1, thus opening the discharge port 12. At this time, since the pressure exerted by the cover plate 26 on the operatively associated cover 20 is removed, the operatively associated cover 20 turns downward under its own weight, thus opening the communication port 17. And with said discharge port 12 and said communication port 17 thus opened, the containers 14 received in the drawer box 15 are discharged downward together with the wastes A.

In the case of the above, since the cover plate 26 is horizontally slid for opening and closing the discharge port 12, the vertical dimension of the sterilizing and crushing apparatus 1 can be reduced as compared with an arrangement designed to move such cover plate 26 vertically to open and close the discharge port 12. In addition, the cover plate 26 may be substantially horizontal.

In addition, the heat insulating box 6, guide rods 23 and cover plate 26 are each formed of a shell 31 of sheet metal and a heat insulating material 32 filled in said shell 31, so that each member has sufficient heat resistance.

In the interior of said casing 2, a crusher 34 is installed below the heat insulating box 6 for crushing said wastes A together with the containers 14. There is provided feeding means 35 for feeding the wastes A together with the containers 14 through said discharge port 12 into the crusher 34, said feeding means 35 being in the form of a chute formed of sheet metal.

In FIG. 1, said crusher 34 comprises a cylindrical crushing case 36 having a transversely extending axis, said crushing case 36 being attached to the carriage 4. The top of the crushing case 36 is formed with a charging port 37, while the bottom of the crushing case 36 is formed with a discharging port 38. The crushing case 36 has fixed cutting blades 39 removably fixed thereto in such a manner that their cutting edges project into the crushing case 36.

Coaxial with said crushing case 36, a rotatable shaft 40 is supported in the crushing case 36 and has a plurality of movable cutting blades 41 projecting therefrom. The rotatable shaft 40 is driven by a driving electric motor 42 in the direction of arrow, as shown, so that the movable cutting blades 41 are rotated together with the rotatable shaft 40.

When wastes A together with the containers 14 are charged through the charging port 37, the fixed cutting blades 39 prevent rotation of said wastes A, while the movable cutting blades 41 dash against said wastes A to crush them. The wastes B thus crushed are discharged downward through the discharging port 38. In this case, said discharging port 38 is covered with a perforated plate 43, so that only part of the crushed wastes B passing through the perforations in said perforated plate 43 are discharged, the remainder being crushed again. A collector box 45 is installed below said perforated plate 43 for collecting said wastes B, said collector box 45 being removably attached to the carriage 4.

Figure 4:
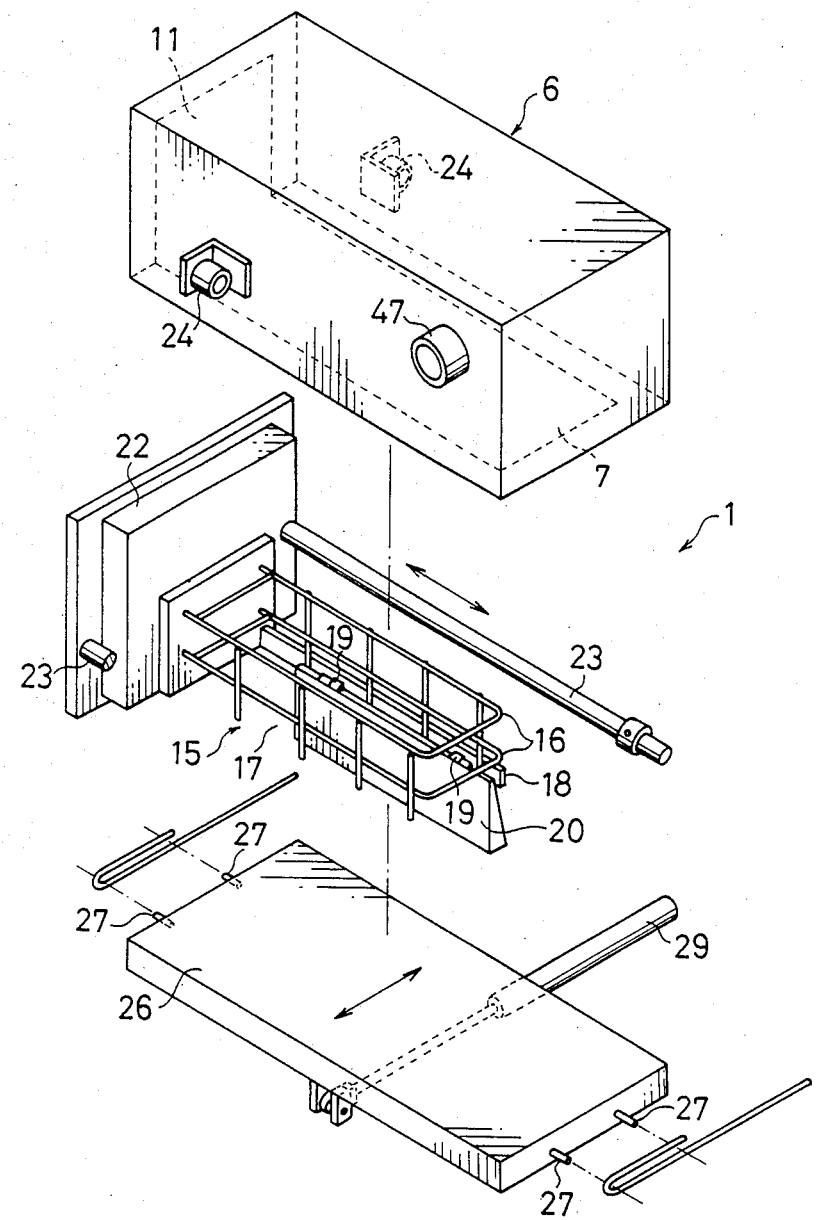

In FIGS. 1 and 4, cooling means 46 is provided for cooling the interior of the heating chamber 7. The cooling means 46 comprises a duct 47 establishing communication between the heating chamber 7 and the outside, and an exhaust fan 48 attached intermediate between the ends of said duct 47. When said exhaust fan 48 is operated, open air is drawn into the heating chamber 7 through a hole (not shown) and the air thus drawn in is discharged to the outside by the exhaust fan 48 through said duct 47. Thereby, the interior of the heating chamber 7 is cooled. That is, the wastes A received in the heating chamber 7 are cooled. The exhaust fan 48 is, for example, a sirocco fan.

The procedures for sterilizing and crushing wastes A will now be described.

Figure 5:
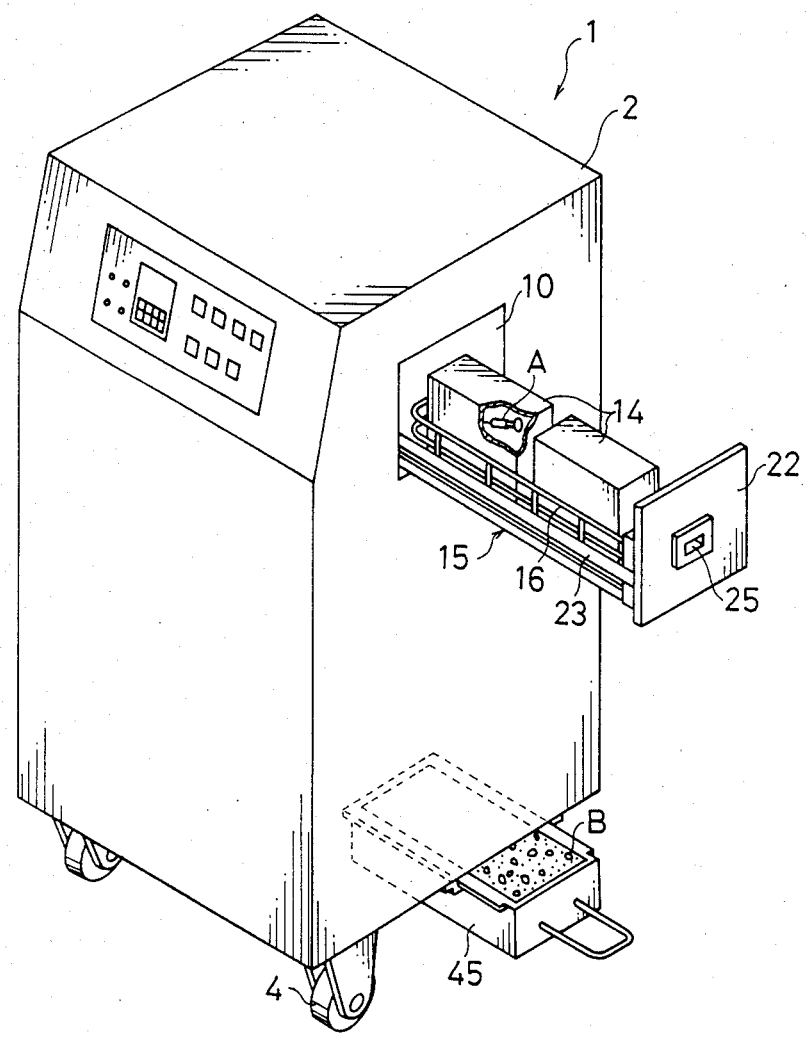

First, the drawer box 15 is drawn out as shown in phantom lines in FIGS. 2 and 3 by the operator's hand gripping the handle 25 shown in FIG. 5. And containers 14 having wastes A received therein are charged into the drawer box 15. Then, the drawer box 15 is pushed into the casing 2 through the inlet opening 10 and insertion port 11. In this case, the cover plate 26 closes the discharge port 12, and in operative association therewith, the operatively associated cover 20 closes the communication port 17.

Subsequently, an operating switch for an unillustrated control unit is turned on, the heater 8 is energized by timer control in accordance with a predetermined program, the energization being maintained for a predetermined period of time so that the wastes A together with the containers 14 in the heating chamber 7 are heated.

In the above case, since the operatively associated cover 20 adapted to support wastes A is formed with a number of through-holes 21, the wastes A are uniformly heated from the exterior. Since the heater 8 is a far infrared heater, it effectively directly heats the wastes A without heating the intermediate layer of air. Therefore, the wastes A are heated to about 15°-250° C. in about 5 minutes after energization Injectors and other objects of glass included in the wastes A are softened in the containers 14 or melted. Further, soft objects containing water, such as rats, are dried as their water is evaporated.

When said temperature is maintained for about 10 minutes, the disease causing germs contained in the wastes A are killed. That is, sterilization is attained without using chemicals. Further, in about 15 minutes after the operating switch has been turned on, the heater 8 is turned off by said timer control In addition, the temperature in the heating chamber 7, including the temperature of the wastes A, is detected by a sensor such as a thermocouple and controlled to be maintained within a predetermined range.

Then, the exhaust fan 48 is operated to cool the wastes A together with the containers 14. The wastes A and the containers 14 are cooled for some minutes to a predetermined temperature of about 50° C. or 70° C. Thus, the temperature conditions for the wastes A and the containers 14 are substantially restored to the original conditions, and they are solidified.

Then, in response to a temperature control signal from an unillustrated sensor, the air cylinder 29 is actuated to cause the cover plate 26 to open the discharge port 12. Thereupon, the operatively associated cover 20 also opens the communication port 17, with the result that the containers together with the wastes A in the drawer box 15 are charged into the crusher 34 successively through the communication port 17, discharge port 12 and feed means 35.

At this time, the driving electric motor 42 is turned on by a discharge detection signal from an unillustrated sensor, so that the crusher 34 is actuated. Thereupon, said wastes A together with the containers 14 are crushed in about 2 or 5 minutes, the crushed wastes B being discharged out of the crusher 34 and collected in the collecting box 45.

In the above case, the glass material, such as injectors, included in the wastes A, is coagulated by cooling, while objects containing water, such as rats, are solidified by drying. Therefore, the crushing conditions are substantially the same for the crusher 34, not differing from wastes A to wastes A, a fact which is preferable for crushing operation. As a result, the wastes A together with the containers 14 are easily crushed in some minutes by the single type of crusher 34. The crushed wastes B have a reduced bulk as compared with the wastes A, so that they can be easily treated for disposal in a land to be reclaimed.

Since the wastes A sterilized in the heating chamber 7 are automatically fed into the crusher 34 through the feeding means and crushed, the sterilizing and crushing of wastes A are performed without the wastes A coming in contact with the operator's hands.

In addition, if the wastes A are injectors, a far infrared heater is used as the heater 8 to heat the wastes A for about 40 minutes. Thereby, the wastes A are heated to about 400° C., so that the disease causing germs adhering to the injectors are killed.

In the case where the wastes A are the dead bodies of experimental animals, such as rats, containing water, a near infrared heater is used as the heater 8 to heat them to about 960° C. Thereupon, the water is evaporated from the wastes A; thus, the wastes A are dried for easier crushing.

The cooling by the cooling means 46 may be such that it lowers the temperature of the wastes A to about 70° C.

Further, the charging of wastes A into the heating chamber 7 may be effected without containers 14.

FIGS. 6 through 10 show a second embodiment of the invention.

In the figures, a sterilizing and crushing apparatus 1 has a casing 51 reinforced by an internal frame 52.

In the upper region of said casing 51, a heat insulating box 53 is obliquely attached to the frame 52. The top of said casing is formed with an inlet opening 54, while the top of said heat insulating box 53 is formed with an insertion port 55 corresponding to said inlet opening 54. Further, the bottom of said heat insulating box 53 is formed with a discharge port 56. Further, a closure lid 57 is provided for closing said inlet opening 54 and insertion port 55.

The lower side of said heat insulating box 53 is formed with an opening 58. This opening 58 is provided with a cover plate 59 adapted to be taken in and out, the lower surface of said cover plate 59 having a pair of slide shafts 60 attached thereto. On the other hand, the frame 52 has a guide plate 61 fixed thereto, said guide plate 61 having a pair of guide rails 62 attached thereto. The slide shafts 60 slide on these guide rails 62. That is, the cover plate 59 slides longitudinally of the guide rails 62.

The slide movement of said cover plate 59 opens and closes the discharge port 56. Further, the heat insulating box 53 is internally provided with a guide frame 64 for receiving a container 14 charged thereinto through the insertion port 55. The upper surface of said cover plate 59 has a frame block 65 attached thereto, so that when the cover plate 59 closes the discharge port 56, the frame block 65 supports the container 14 in the guide frame 64. One end of the cover plate 59 is integrally formed with a lid 66, so that when the cover plate 59 closes the discharge port 56, the lid 66 closes the opening 58.

The guide plate 61 is formed with an opening 67 through which extends a bracket 68 projecting from the lower surface of said cover plate 59, said bracket 68 having one end of a rack gear 69 connected thereto. Attached to the lower surface of said guide plate 61 are a pinion gear 70 and an electric motor 71 for driving said pinion gear 70. The rack gear 69 meshes with the pinion gear 70.

Figure 6:
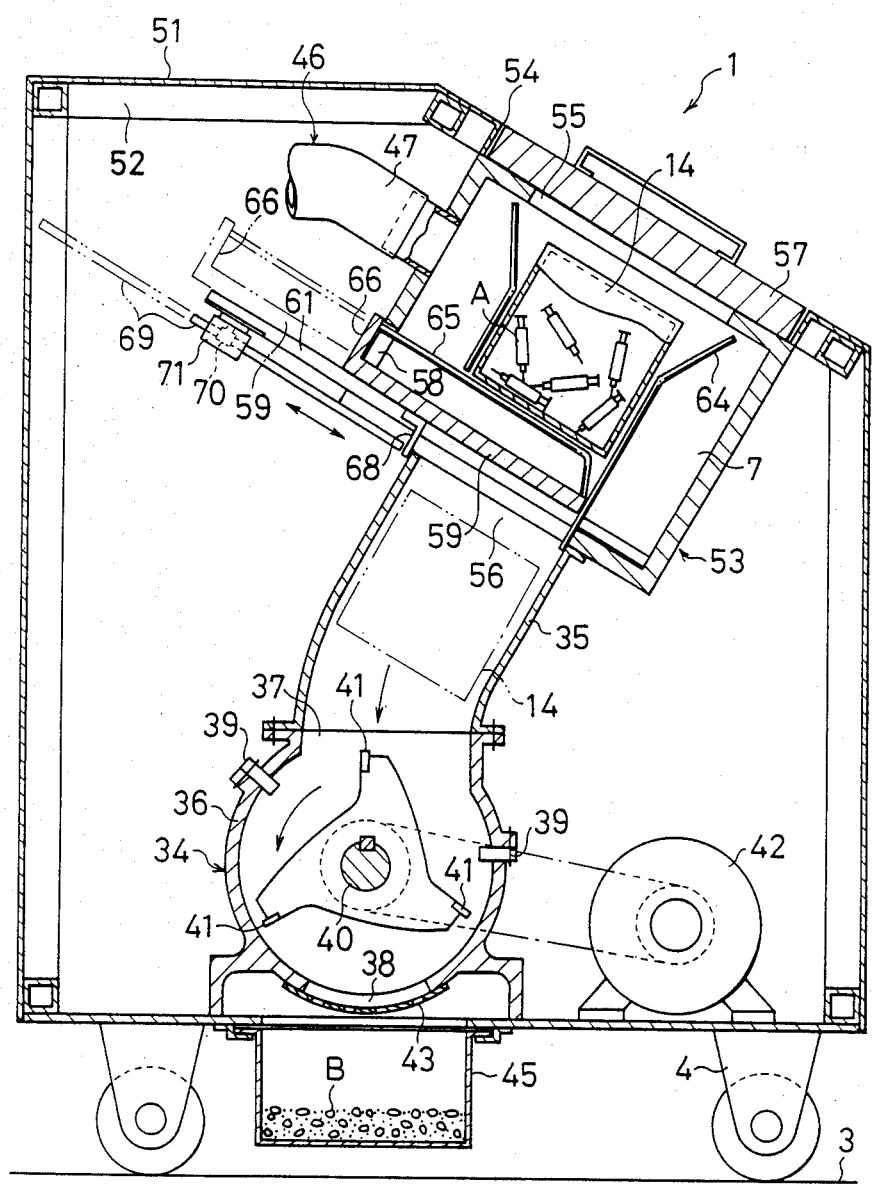
FIGS. 6 through 10 show a second embodiment of the invention.
Figure 7:
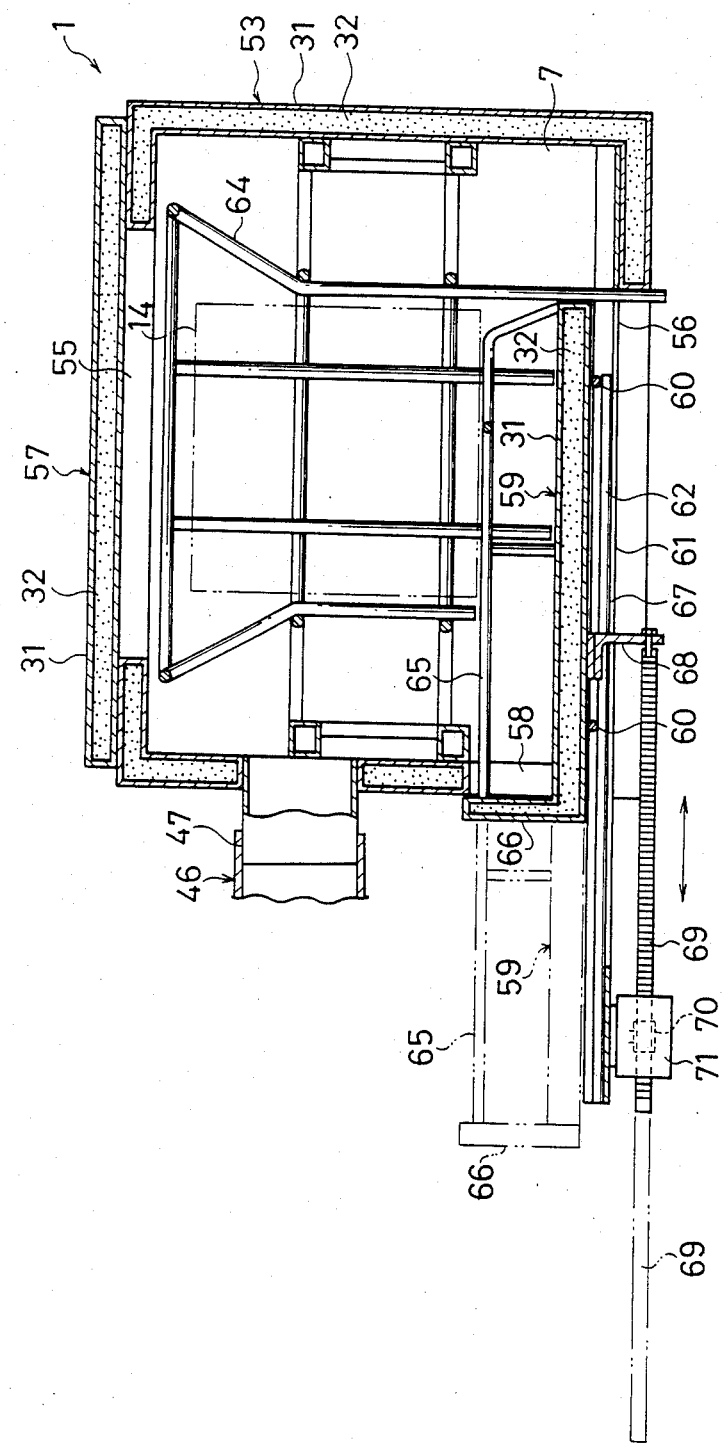
Figure 8:
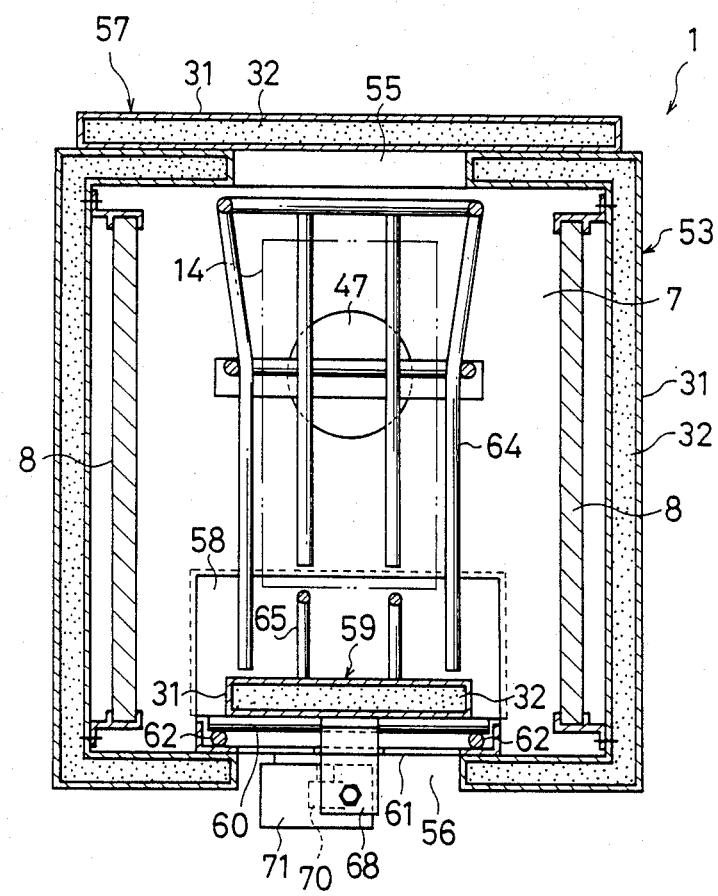
Figure 9:
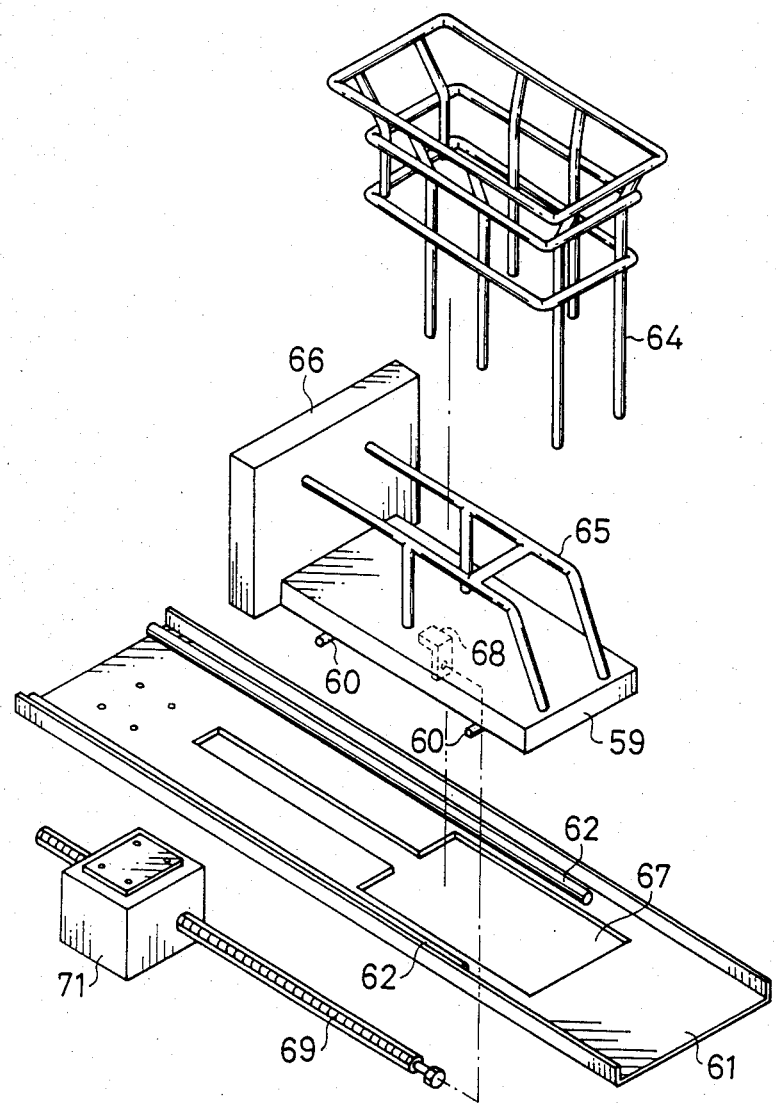
Figure 10:
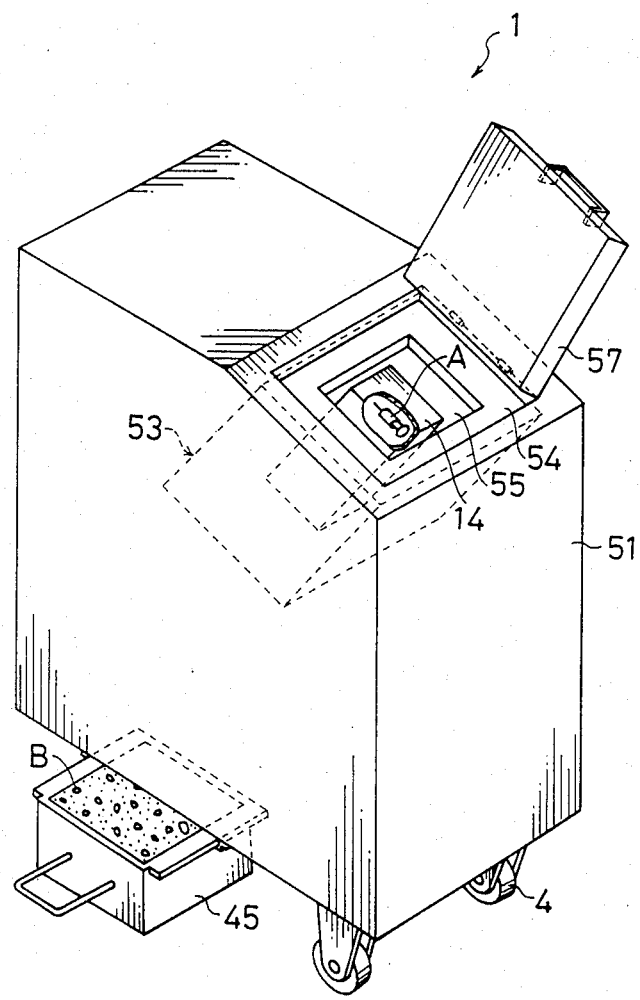

When the electric motor 71 is actuated to rotate the pinion gear 70 in one direction, the rack gear 69 operatively associated with the pinion gear 70 causes the cover plate 59 to close the discharge port 56, as shown in solid lines in FIGS. 6 and 7.

On the other hand, when the pinion gear 70 is rotated in the opposite direction by the actuation of the electric motor 71, the rack gear 69 operatively associated with said pinion gear 70 causes the cover plate 50 to open the discharge port 56, as shown in phantom lines in FIGS. 6 and 7.

Thereupon, the container 14 together with the wastes A in the guide frame 64 is discharged to the feeding means 35. In this case, the rack gear 69, pinion gear 70 and electric motor 71 constitute driving means for sliding the cover plate 59.

In addition, the heater 8, crusher 34, collecting box 45, cooling means 46 and other arrangements are the same in control and operation as those of the first embodiment described above.

FIGS. 11 through 14 show a third embodiment of the invention.

In the figures, a sterilizing and crushing apparatus 1 has a casing 73. The casing 73 is internally provided with a heat insulating box 74 which is internally divided into 6 heating chambers 75, three on each of the opposite sides, by partition walls 74a. Each heating chamber 75 has a heater 8. Further, each heater 8 is provided with a protector frame 74b for preventing the wastes A and container 14 from contacting the heater 8. The surface of the protector frame 74b is coated with a coating material, such as silicone rubber, which has heat resistance to withstand the highest temperature (about 1,000° C.) in the heating chamber 75, and non-viscosity which enables the synthetic resin, included in the wastes A having increased viscosity due to heating, to easily separate therefrom.

The top of the casing 73 is formed with an inlet opening 76 and a slide shutter 77 is provided for opening and closing said inlet opening 76. The top of said heat insulating box 74 is formed with insertion ports 78 each associated with one of said heating chambers 75, and common lids 79 are provided each for opening and closing two adjacent insertion ports 78. And after the insertion port 76 has been opened by the shutter 77, the lids 79 are turned upward as shown in phantom lines in FIG. 12 to open the insertion ports 78, whereupon it becomes possible to insert containers 14 together with wastes A into the heating chambers 75.

On the other hand, the bottom of each heating chamber 75 is formed with a discharge port 80. A cover plate 82 is provided for opening and closing said discharge port 80, the upper surface of said cover plate 82 being coated with the coating material described above. The cover plates 82 are pivotally supported for vertical turning movement on the heat insulating box 74, and an electrically powered cylinder 83 is provided for vertically turning each cover plate 82.

Figure 11:
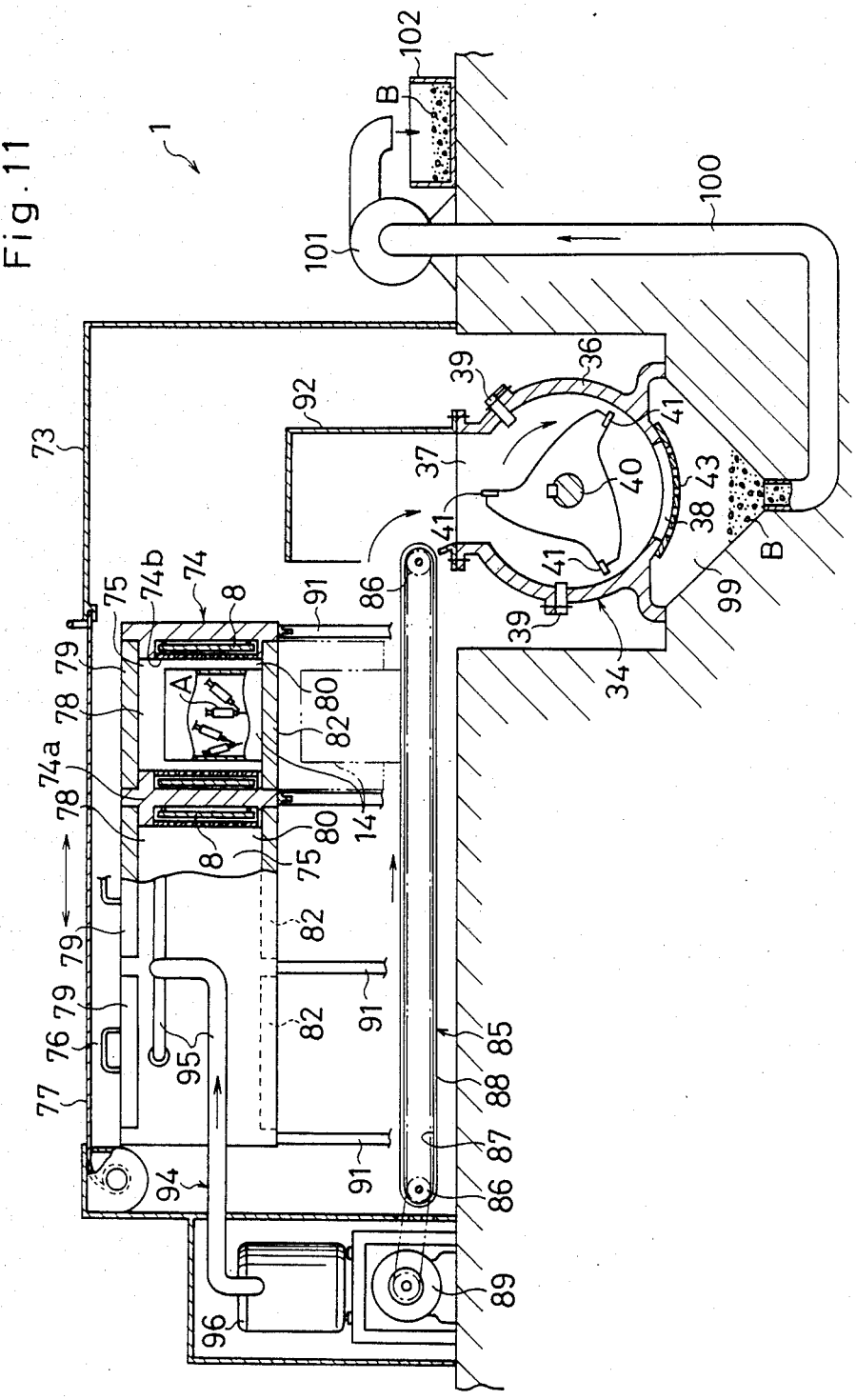
FIGS. 11 through 14 show a third embodiment of the invention.
Figure 12:
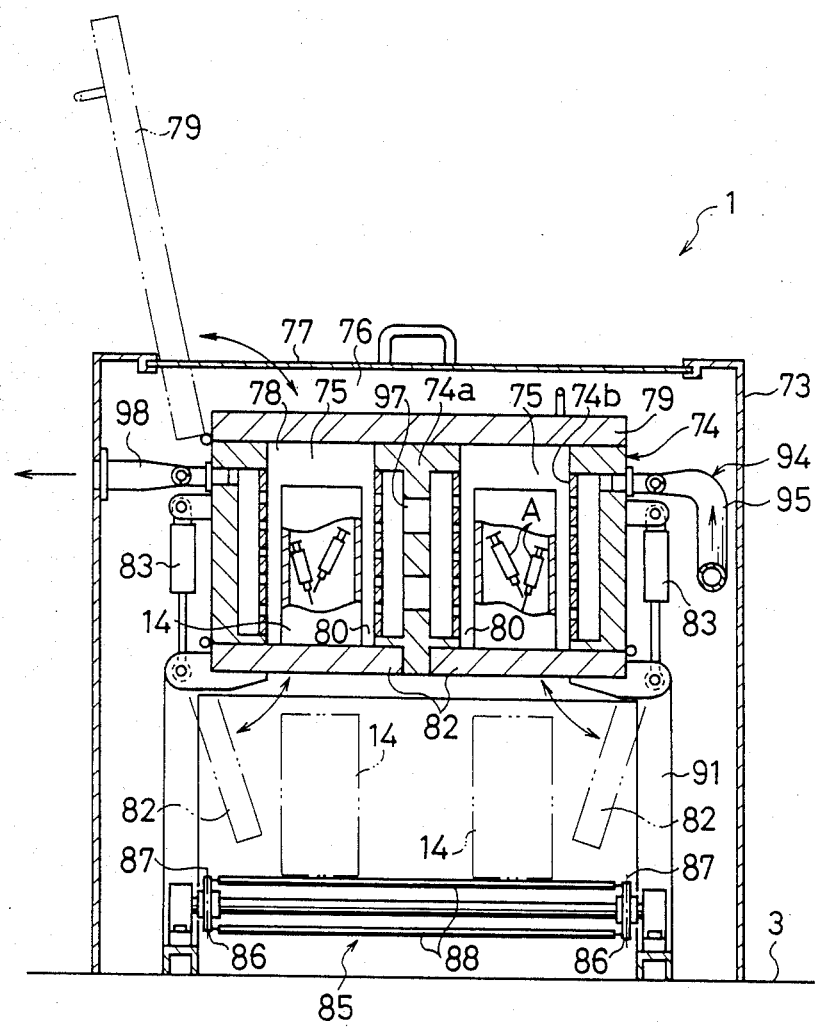
Figure 13:
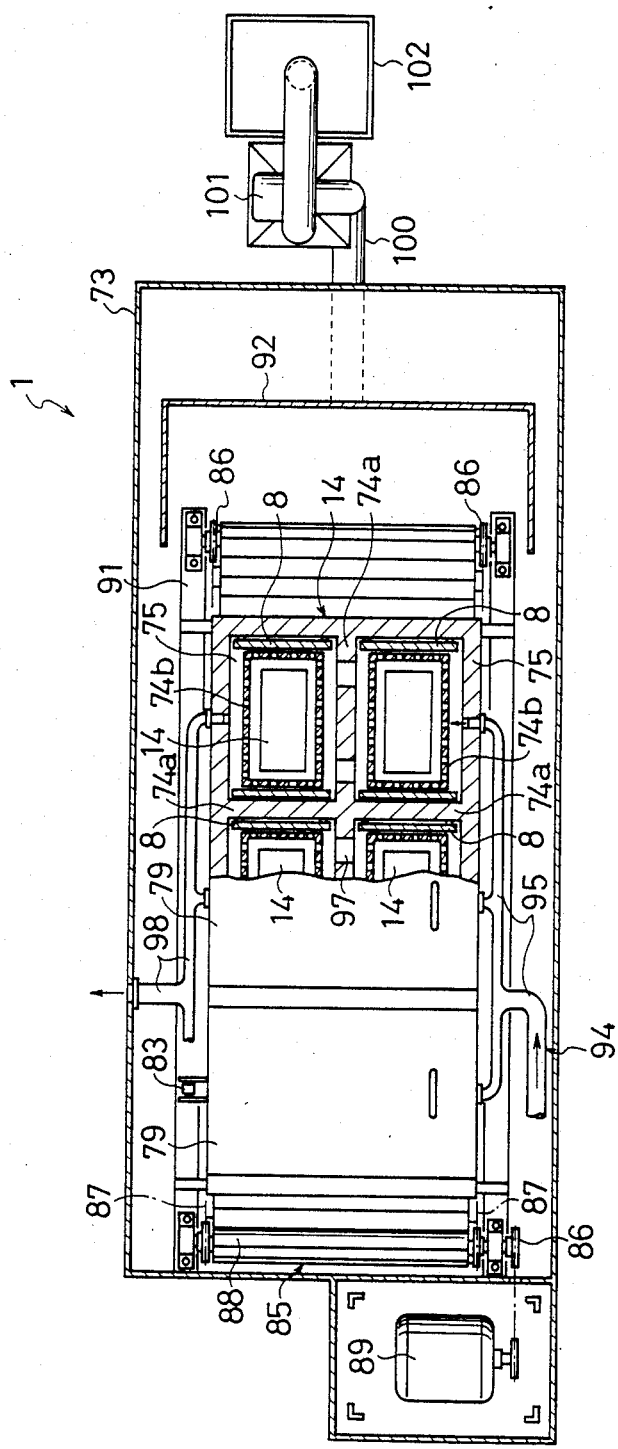
Figure 14:
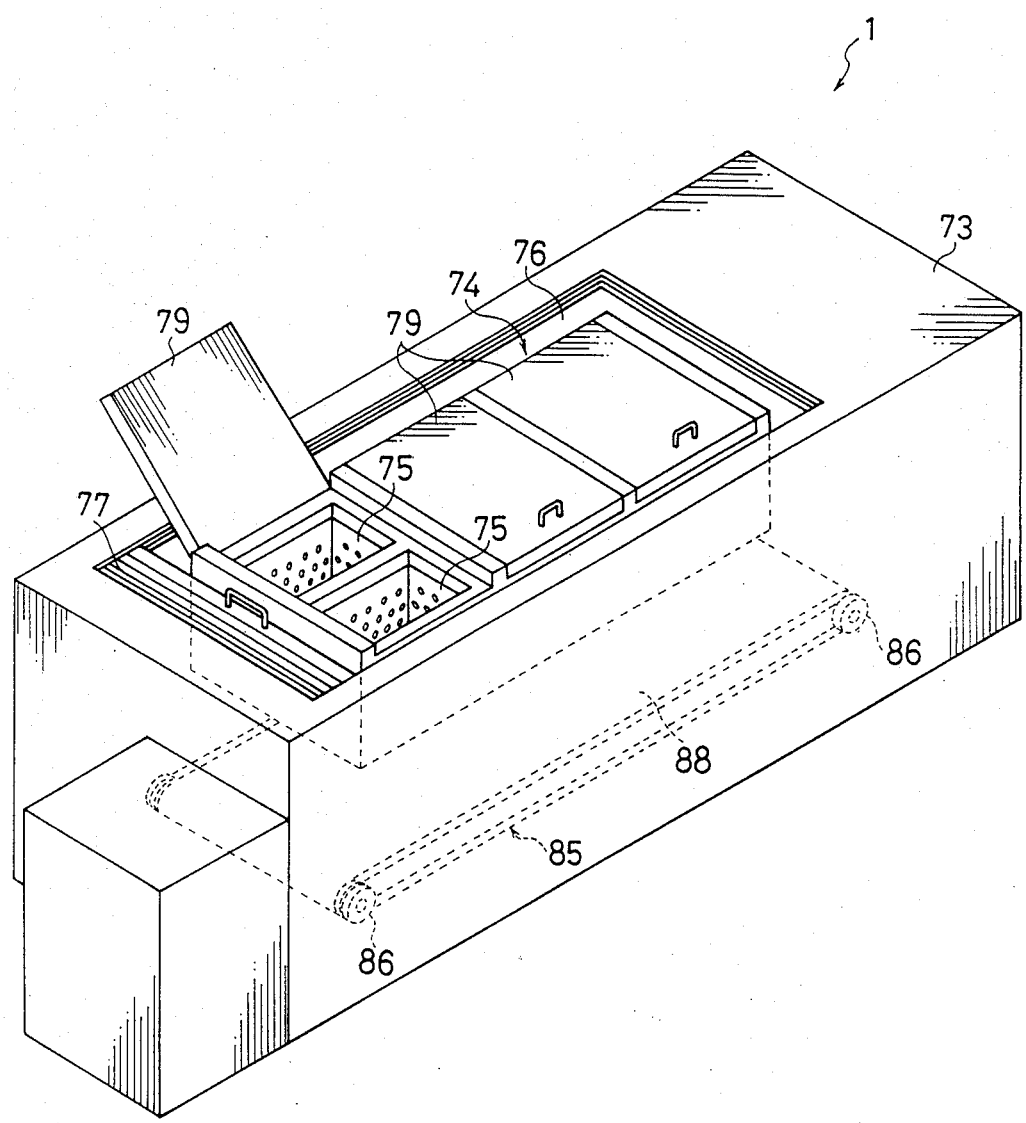

When the electrically powered cylinders 83 are actuated to turn the cover plates 82 upward, as shown in solid lines in FIGS. 11 and 12, the discharge ports 80 are closed to make it possible to receive wastes A together with containers 14 in the heating insulating box 74. On the other hand, the operation of said electrically powered cylinders 83 also causes the cover plates 82 to turn downward, whereupon the containers 14 in the heat insulating box 74 together with the wastes A are discharged downward through said discharge ports 80.

In FIGS. 11 through 14, feeding means 85 is positioned below said heat insulating box 74. The feeding means 85 is in the form of a conveyor which feeds said containers 14 together with wastes A laterally into the crusher 34. The feeding means 85 comprises a pair of sprocket wheels 86, a pair of chains 87 entrained around said sprocket wheels 86, and a steel slat 88 installed on the chains 87. An electric motor 89 is provided for driving said slat 88 in the direction of arrow 11, said slat 88 being adapted to transfer wastes A having a high temperature.

In the above case, even if wastes A are simultaneously discharged from the respective discharge ports 80, they are successively fed into the crusher 34 by the feeding means 85. Therefore, the crusher 34 is prevented from being overloaded.

The numeral 91 in FIG. 11 denotes a support block supporting the heat insulating box 74, and 92 denotes a dust protective cover.

The cooling means 94 comprises an air feed pipe 95 establishing communication between the exterior of the casing 73 and the heating chamber 75, and a fan 96 for feeding air into the heating chamber 74 through said air feed pipe 95. The air fed into a heating chamber 75 is also fed into the next heating chamber 75 through through-holes 97 formed in the partition wall 74a, as shown in FIG. 12. An exhaust pipe 98 extends from the heating chamber 75 to the outside of the casing 73, so that the air which has cooled the interior of each heating chamber 75 is discharged through said exhaust pipe 98.

The containers 14 and wastes A crushed by the crusher 34 are once collected in a dust collecting hopper 99, from which they are drawn up into a dust collecting fan 101 through an air feed pipe 100 and finally into a dust collecting box 102.

In addition, the heater 8, crusher 34, dust collecting box 45, cooling means 46 and other arrangements are the same in control and operation as those of the first embodiment.

What is claimed is:

1. A waste sterilizing and crushing apparatus comprising a heating chamber adapted to receive wastes; a heater for heating the interior of said heating chamber; a discharge port formed in the bottom of said heating chamber for downwardly discharging the wastes received in said heating chamber; a cover plate driven by drive means to open and close said discharge port; a crusher disposed below said heating chamber for crushing the wastes; and feeding means whereby the wastes discharged through said discharge port are fed into said crusher.

2. A waste sterilizing and crushing apparatus as set forth in claim 1, including a drawer box making it possible to charge wastes, the lateral wall of said heating chamber being formed with an insertion port through which said drawer having wastes charged thereinto is taken in and out, the bottom of said drawer box being formed with a communication port corresponding to the discharge port of the heating chamber, an operatively associated cover plate operatively associated with the cover plate to open and close said communication port, said drawer box having a lid attached thereto which is adapted to close the insertion port when said drawer box is inserted into the heating chamber.

3. A waste sterilizing and crushing apparatus as set forth in claim 1, wherein cooling means is provided which introduces open air into the heating chamber and which discharges the air fed into said heating chamber.

4. A waste sterilizing and crushing apparatus as set forth in any one of claims 1, 2 or 3, wherein the cover plate is adapted to be horizontally driven to open and close the discharge port.

5. A waste sterilizing and crushing apparatus as set forth in any one of claims 1, 2 or 3, wherein the heating chamber is divided into a plurality of heating chambers, each heating chamber having a heater attached thereto.

6. A waste sterilizing and crushing apparatus as set forth in claim 5, wherein the feeding means is a feeding conveyor for transversely conveying wastes.

* * * * *